US006948493B2

(12) United States Patent
Dunlop (10) Patent No.: US 6,948,493 B2
(45) Date of Patent: Sep. 27, 2005

(54) ANAESTHETIC APPARATUS (76) Inventor: Colin Dunlop, 132A Cressy Road, East Ryde, New South Wales 2113 (AU)

( * ) Notice: Subject to any disclaimer, the term of this patent is extended or adjusted under 35 U.S.C. 154(b) by 29 days.

(21) Appl. No.: 10/168,052
(22) PCT Filed: Dec. 15, 2000
(86) PCT No.: PCT/AU00/01548
§ 371 (c)(1),
(2), (4) Date: Oct. 3, 2002
(87) PCT Pub. No.: WO01/43803
PCT Pub. Date: Jun. 21, 2001

(65) Prior Publication Data
US 2003/0140922 A1 Jul. 31, 2003

(30) Foreign Application Priority Data
Dec. 15, 1999 (AU) .............................................. PQ4669

(51) Int. Cl.[7] ........................ A61M 15/00; A61M 16/10
(52) U.S. Cl. ............................. 128/203.12; 128/200.11; 128/202.27; 128/204.14; 128/911; 128/912
(58) Field of Search ....................... 128/200.11, 200.24, 128/202.27, 203.12, 203.6, 204.14, 204.18, 204.25, 205.17, 911–912

(56) References Cited

U.S. PATENT DOCUMENTS

| 4,061,160 A | | 12/1977 | Kashmer et al. ......... 137/637.2 |
| 4,188,946 A | * | 2/1980 | Watson et al. ......... 128/204.22 |
| 4,232,666 A | | 11/1980 | Savelli et al. ......... 128/203.25 |
| 4,265,239 A | * | 5/1981 | Fischer et al. ......... 128/205.17 |
| 4,621,634 A | * | 11/1986 | Nowacki et al. ....... 128/204.18 |
| 4,637,384 A | * | 1/1987 | Schroeder .............. 128/204.18 |
| 5,121,746 A | * | 6/1992 | Sikora .................... 128/203.12 |
| 5,549,105 A | * | 8/1996 | Bloch et al. ........... 128/203.12 |
| 5,558,088 A | * | 9/1996 | Smith .................... 128/205.28 |
| 5,568,910 A | | 10/1996 | Koehler et al. ................ 251/83 |
| 5,664,563 A | * | 9/1997 | Schroeder et al. ..... 128/204.25 |
| 5,682,876 A | * | 11/1997 | Pernetti et al. ........ 128/202.27 |
| 5,735,267 A | * | 4/1998 | Tobia .................... 128/204.21 |
| 5,743,257 A | * | 4/1998 | Koehler et al. ........ 128/205.24 |
| 5,806,513 A | * | 9/1998 | Tham et al. ........... 128/204.22 |
| 5,988,164 A | * | 11/1999 | Paluch .................. 128/203.26 |
| 6,021,777 A | | 2/2000 | Post et al. ............. 128/204.13 |
| 6,286,505 B1 | * | 9/2001 | Psaros ................... 128/203.12 |
| 6,536,430 B1 | * | 3/2003 | Smith .................... 128/204.18 |
| 6,571,792 B1 | * | 6/2003 | Hendrickson et al. . 128/203.12 |

FOREIGN PATENT DOCUMENTS

| EP | 0 903 160 A1 | 3/1999 | .......... A61M/16/08 |
| GB | 2 170 109 A | 7/1986 | .......... A61M/17/00 |
| GB | 2 269 762 A | 2/1994 | .......... A61M/15/06 |

* cited by examiner

Primary Examiner—Henry Bennett
Assistant Examiner—Amanda Wieker
(74) Attorney, Agent, or Firm—Davis & Bujold, P.L.L.C.

(57) ABSTRACT

An apparatus for delivering anaesthetic to human or animal patients. The apparatus is an anaesthetic machine which is arranged to mount components of an anaesthetic delivery circuit, and which includes a collector arrangement in the form of a manifold having a plurality of inlets and outlets. The manifold enables a reduction in the number of tubes connecting the various components in an anaesthetic system, which are normally required in prior art anaesthetic machines. The manifold also includes an arrangement which provides a Venturi effect on gas flow, and enables a pressure gauge to be mounted out of a patient breathing circuit. The machine is preferably portable.

12 Claims, 8 Drawing Sheets

ANAESTHETIC APPARATUS

FIELD OF INVENTION

The present invention relates generally to an apparatus for delivering anaesthetic to a human or animal patient, and in particular to an anaesthetic apparatus facilitating the delivery of inhalation anaesthetics.

BACKGROUND OF INVENTION

Inhalation anaesthetics are drugs that are breathed into the lungs and from there absorbed into the blood. Inhalation anaesthetics are either gases (such as nitrous oxide, helium, etc) or vapours. Vapours are usually produced by volatile liquids, which primarily exist as a liquid at room temperature. Inhalation anaesthetic agents that are vapours include halothane, isoflurane, enflurane and sivoflurane.

To facilitate administration of anaesthetic vapours, it is usually necessary to encourage the liquid to form a vapour or gas. This vapour is administered in a controlled fashion to an anaesthetic breathing circuit, and therefore to the patient. The devices which hold the liquid anaesthetic and produce a vapour are called anaesthetic vaporisers. Anaesthetic vapour is collected from the vaporiser and delivered to the anaesthetic breathing circuit using oxygen, which is required to sustain the life of the patient. The oxygen flows through the anaesthetic vaporiser and carries the vapour to the anaesthetic breathing circuit.

Anaesthetic vaporisers must perform predictably and must be capable of delivering accurate, controlled dosages of anaesthetic vapour to the anaesthetic breathing circuit. For example, the anaesthetic dose of halothane which is administered to the lungs is between 1% and 2%. The lethal dose of halothane is around 3%–4%. It is therefore important that anaesthetic vaporisers are maintained and not subject to conditions which may damage them and render their output inaccurate.

Anaesthetic circuits vary in type. The aim is to deliver a controlled amount of anaesthetic and oxygen to a patient. Circuits include "rebreathing" systems which contain valves and soda lime (which removes the carbon-dioxide exhaled by the patient, so that the exhaled gas can be re-breathed) or non-rebreathing systems which have no soda-lime and where all exhaled gases are exhausted (eg T pieces, Bain circuits, Norman elbows).

Any anaesthetic delivery system will usually include a number of elements, as follows:

Oxygen supply, usually in the form of a pressurised vessel, with a regulator, for providing oxygen to the anaesthetic system; an oxygen flow meter for monitoring oxygen flows; a vaporiser connected in the oxygen flow line providing anaesthetic to the anaesthetic breathing circuit; an oxygen flush valve and lines to bypass the vaporiser to provide pure oxygen to the patient without anaesthetic; a pressure gauge to indicate the pressure in the patient's breathing circuit; various gas lines connecting together all the components in the circuit.

Some or all of these components may be mounted to a support structure, forming what is known as an "anaesthetic machines". This support may provide mountings for the flow meter, the vaporiser and also mountings for the various gas lines connecting the anaesthetic delivery system. Anaesthetic machines tend to be of two types. A first type are large machines mounted on four wheel trolleys, usually with all components enclosed, and typically found in hospital surgeries. A second type is small machines which are portable and can be hand carried or fitted to a small mobile stand. One problem with present arrangements of portable anaesthetic machines is that because there are a number of relatively long gas flow lines, many of which remain exposed, they could become tangled and could even be pulled out during operation or transport of the system. This is dangerous. Further, any anaesthetic machine which has exposed gas lines is difficult to transport either to end user or between hospitals or after sale service of machine (eg to the end user after sale or service of the machine) without damage, as well as being inconvenient to use.

SUMMARY OF INVENTION

The present invention provides, from a first aspect, a connector arrangement for an anaesthetic delivery system, the connector arrangement comprising a manifold including at least one inlet and a plurality of outlets, the at least one inlet and the plurality of outlets being arranged for connection to gas lines in the anaesthetic circuit, whereby the manifold facilitates minimising the extent of gas line components required in the anaesthetic circuit.

The manifold preferably comprises a plurality of inlets. Preferably, the manifold includes a first, high pressure portion, including an oxygen inlet for receiving oxygen from an oxygen supply and regulator, and an oxygen outlet for providing oxygen to an oxygen flow meter, and a second, low pressure portion, having a vaporiser inlet for receiving oxygen and anaesthetic from the vaporiser and a patient outlet for providing oxygen/anaesthetic mixture to a patient breathing circuit.

Provision of such a manifold preferably enables the reduction of the extent of gas lines and complexity of gas line connection components over prior art anaesthetic systems and preferably enables the provision of an anaesthetic machine incorporating the manifold in which there are no exposed gas lines or the exposure of gas lines is minimised, and the complexity of servicing is reduced as the extent of connecting gas lines is reduced.

The connector arrangement of the present invention may be used with either type (portable or non-portable) anaesthetic machine, but has particular advantage in use with the portable machine. It advantageously facilitates the production of a portable machine which can be used in veterinary surgery applications, and also a portable machine which can be used for human anaesthesia applications, e.g. which may be used on an ambulance or which may have military (field hospital) applications.

Preferably, the manifold is an integrated body incorporating conduits connecting the inlets and outlets. The manifold therefore, preferably provides a single body which effectively replaces multiple components connecting gas lines in prior art anaesthetic supply circuits.

Preferably, an oxygen flush outlet is provided in the manifold for connection to a flush valve and an oxygen flush inlet is provided for connection from the flush valve, thereby providing a flush bypass line, for oxygen to be provided directly to the patient outlet and thereby to the patient, bypassing the vaporiser.

A further problem with prior art anaesthetic supply circuits is the possibility of causing damage to the anaesthetic vaporiser when the flush valve is operated to bypass the vaporiser and provide oxygen directly to the patient. Because oxygen is provided directly from the high pressure end of the circuit in this case (ie from a line connected to the regulator and oxygen supply tank), high pressure oxygen can inadvertently flow back along the vaporiser patient line to the outlet of the vaporiser, affecting vaporiser performance and sometimes causing damage. As anaesthetic vaporisers are very delicate and performance and accuracy is important, even minor back pressure can alter performance damage can cause major problems (inaccurate vaporiser can cause accident and even death).

Preferably, the manifold includes in the low pressure portion connected to the oxygen flush inlet a Venturi arrangement, preferably in the form of a "Venturi" injection orifice, the injection orifice being placed adjacent to a conduit connected to the vaporiser inlet, whereby a Venturi effect occurs, maintaining relatively low pressure in the conduit from the vaporizer inlet.

Preferably, therefore, when the flush valve is operated, the Venturi effect provided by the Venturi injection orifice in its position with respect to the vaporiser inlet, maintains relatively low pressure in the line back to the outlet of the vaporiser. There is therefore preferably no flow of a relatively high pressure oxygen to the outlet of the vaporiser during flush operation, and therefore no back pressure effect or damage to the vaporiser.

The Venturi arrangement also preferably enables a pressure gauge for monitoring the pressure of the patient's breathing circuit to be mounted outside the breathing circuit and be connected to the vaporiser inlet of the manifold. Normally, it is necessary to mount the pressure gauge in the patient breathing circuit, to avoid the possibility of damage on operation of the flush valve. The Venturi arrangement preferably dispenses with this need and the pressure gauge can be mounted out of the patient breathing circuit. This has the advantage that a single pressure gauge can be used for both rebreathing and non-rebreathing patient breathing circuits, whereas in the prior art it is usually necessary to use separate pressure gauges.

In a preferred embodiment of the present invention, the vaporiser includes a universal outlet on which the pressure gauge is directly mounted.

Preferably, the manifold also includes an additional oxygen outlet, which can be used for providing oxygen from the line from the regulator and oxygen tank, to an additional flow meter for an additional patient breathing circuit or to an anaesthetic ventilator. This feature would be particularly advantageous in a small or temporary clinic facility where oxygen may not be piped to every bedside. This can enable the same anaesthetic system to be used for two patients as could, for example, occur during a caesarean section when the mother is breathing from the anaesthetic circuit and the infant might require oxygen via eg a face mask immediately after delivery.

Anaesthetic machine design and standardisation has resulted in a variety of breathing circuit designs and connectors being available in different countries. Preferably, the patient outlet is formed as a "universal" outlet which allows connection of a plurality of standard connectors.

The present invention further provides, from a second aspect, an anaesthetic machine comprising a housing including means for mounting components of an anaesthetic delivery system, and including a connector arrangement in accordance with the preceding aspect of the invention discussed above.

Because of the provision of the connector arrangement in the anaesthetic machine, the extent of gas lines required can preferably be minimised.

The present invention yet further provides, from a third aspect, an anaesthetic machine comprising a housing, including means for mounting components of an anaesthetic delivery system, the housing comprising a base, a back wall and a top wall extending over the base, the base, back wall and top wall forming an enclosure and the means for mounting the components being within the enclosure, whereby any gas lines required to connect the components mounted in the enclosure run within the enclosure.

Preferably therefore, the enclosure operates to protect components and gas lines connecting the component from accidental damage.

Preferably, a connector arrangement in accordance with the first aspect of the invention is mounted within the enclosure.

Preferably, an anaesthetic machine of the second aspect of the invention discussed above also includes a housing forming an enclosure in accordance with the third aspect of the invention discussed above.

Preferably, in both the second and third aspects of the invention, the means for mounting includes means for mounting a vaporiser within the enclosure, and also preferably a flow meter within the enclosure.

Preferably, the wrap around top shelf enables the manifold to be mounted in an elevated position, to facilitate attachment of patient circuits where the breathing tubes and other components may need to be elevated. Note that the present apparatus can be used with any type of circuit and is not limited to the patient circuits illustrated in the drawings and described in the description.

Preferably, the anaesthetic machine also includes means for mounting a pressure gauge, which is preferably mounted out of the patient breathing circuit, as discussed in relation to the first aspect of the invention discussed above.

The present invention yet further provides, in an anaesthetic delivery system comprising a vaporiser connectable to an oxygen supply and a patient breathing circuit, for providing a mixture of oxygen and anaesthetic to the patient breathing circuit, and a flush bypass system for bypassing the vaporiser to provide oxygen directly to the patient breathing circuit, a method of avoiding relatively high pressure oxygen being provided back to the vaporiser from the flush bypass system on operation of the flush bypass system, comprising the step of employing the Venturi effect to maintain relatively low pressure in a line from the vaporiser to a connection with the flush bypass system.

The present invention further provides, in an anaesthetic delivery system comprising a vaporiser connectable to an oxygen supply and a patient breathing circuit, for providing a mixture of oxygen and anaesthetic to the patient breathing circuit, and a flush bypass system for bypassing the vaporiser to provide oxygen directly to the patient breathing circuit, an arrangement for avoiding relatively high pressure oxygen being provided back to the vaporiser from the flush bypass system on operation of the flush bypass system, comprising at a connection between a line from the vaporiser and the flush bypass system, a Venturi arrangement which, when the flush bypass is actuated, operates to maintain relatively low pressure in a line from the vaporiser, substantially avoiding high pressure oxygen flowing into that line and back to the vaporiser.

With the above arrangement, preferably the anaesthetic delivery system also includes a pressure gauge, which is preferably mounted out of the patient's breathing circuit and preferably connected to the line between the vaporiser and the flush bypass system.

Preferably, the pressure gauge is mounted directly to the vaporiser outlet, preferably via a universal connector.

BRIEF DESCRIPTION OF DRAWINGS

Features and advantages of the present invention will become apparent from the following description of an embodiment thereof, by way of example only, with reference to the accompanying drawings, in which.

DESCRIPTION OF PREFERRED EMBODIMENTS

Figure 1:
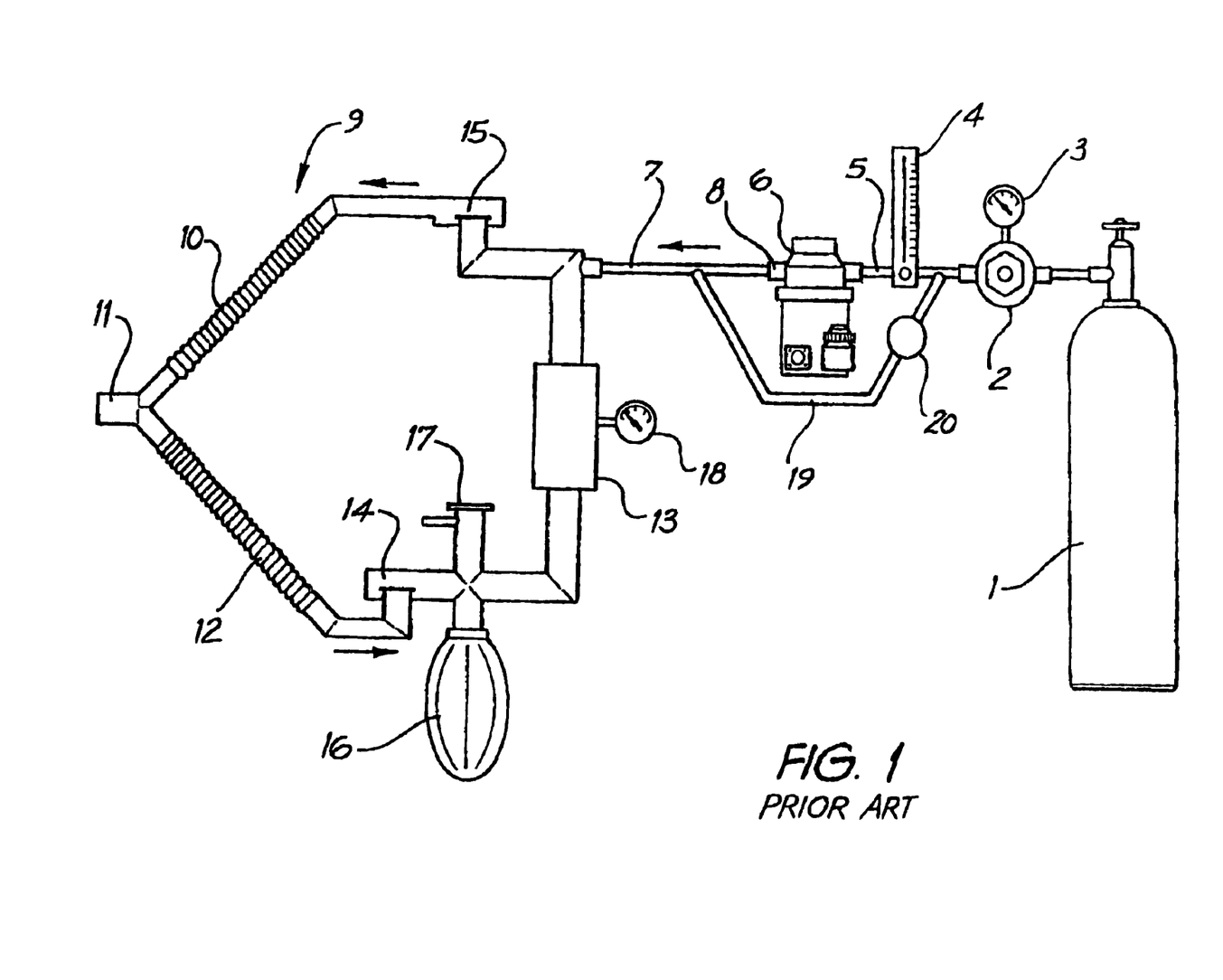
FIG. 1 is a schematic diagram illustrating a prior art anaesthetic delivery system.

Referring to FIG. 1, a prior art anaesthetic delivery system is illustrated. The delivery system includes a pressurised source 1 of oxygen, a regulator 2 for regulating the supply of oxygen from the source 1 and a pressure gauge 3 for monitoring oxygen pressure. Flowmeter 4 is connected in a line 5 from the regulator 2 to an anaesthetic vaporiser 6. Anaesthetic vaporiser 6 may be of any known type which can provide anaesthetic vapour to the anaesthetic supply system. The gas line 7 connects the outlet 8 of the vaporiser 6 to a patient circuit designated generally by a reference numeral 9 which, in this case, is a rebreathing type circuit. The rebreathing circuit 9 comprises a gas line 10 providing anaesthetic oxygen mixture to a line 11 to the patient. A mask or endotracheal tube (not shown) will usually be connected to the line 11 in order to delivery the anaesthetic oxygen mixture to the patient. A return line 12 receives waste gases from the patient. These are conveyed via vessel 13 which contains soda lime for removing carbon dioxide from the waste gases so that the gases can be rebreathed. Non return valves 14, 15 ensure that gas flow direction in the rebreathing circuit 9 is one way. The rebreathing circuit 9 also includes a reservoir or rebreathing bag 16 which provides a variable storage volume to compensate for variations in sizes of breath for each patient. It also allows for positive ventilation. A "pop-off" valve 17 is also provided for relieving pressure in the circuit if necessary. A pressure gauge 18 is provided to indicate the pressure in the patient rebreathing circuit 9. A flush bypass system, in this example, comprising a bypass line 19 and flush valve 20, is provided to bypass the vaporiser 6 and provide pure oxygen to the circuit 9 on operation of the flush valve 20.

This prior art circuit has the problems which are discussed in the preamble of this specification. These include the fact (in portable machines, in particular) that the lines 19, 5, 6, usually exposed, can easily get in the way and become damaged and tangled. Operation of the flush valve 20 can lead to high pressure oxygen being provided to the outlet 8 of the vaporiser causing damage to the delicate components of the vaporiser.

Figure 2:
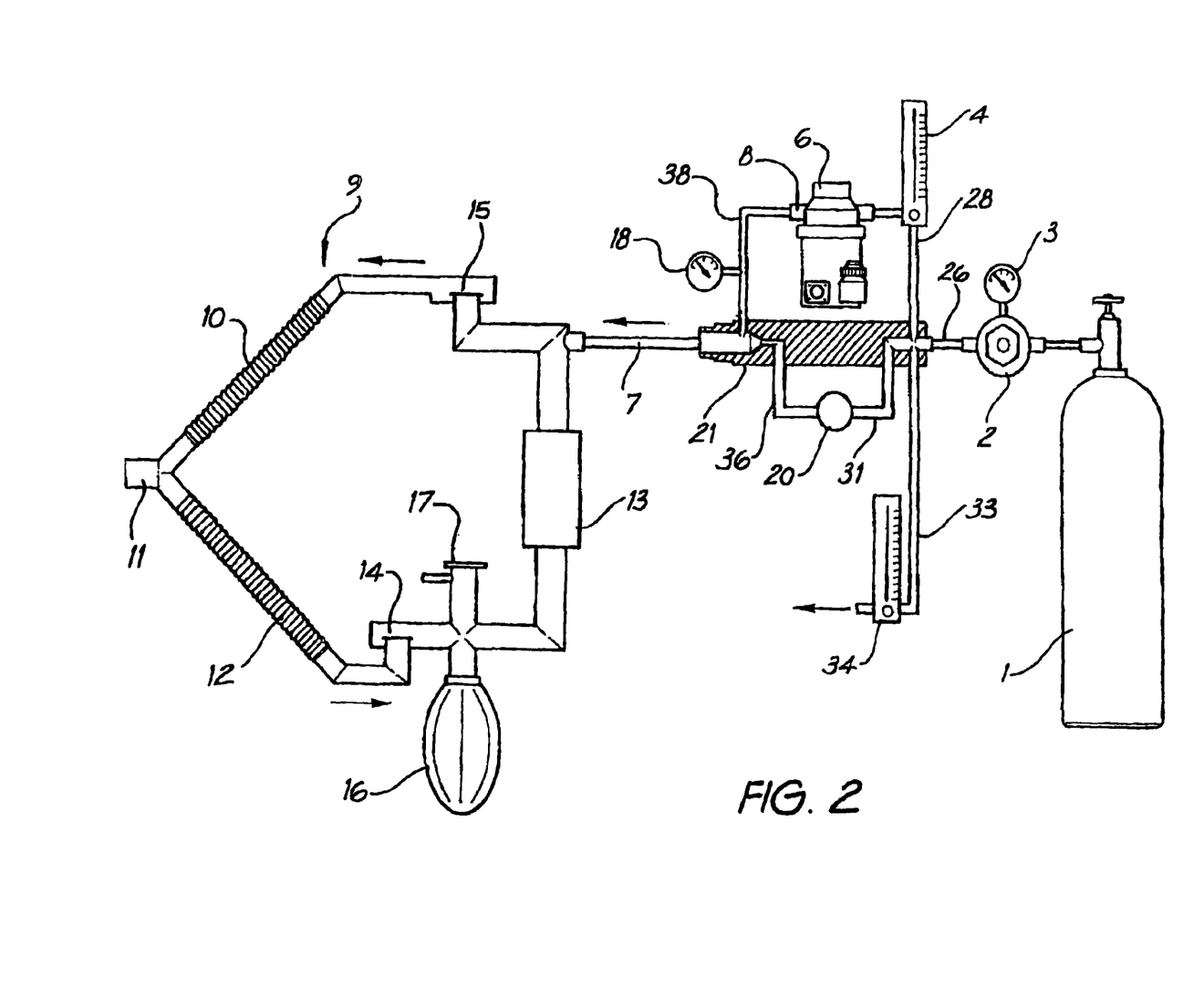
FIG. 2 is a schematic diagram illustrating an anaesthetic delivery system employing a connector arrangement in accordance with an embodiment of the present invention.
Figure 3:
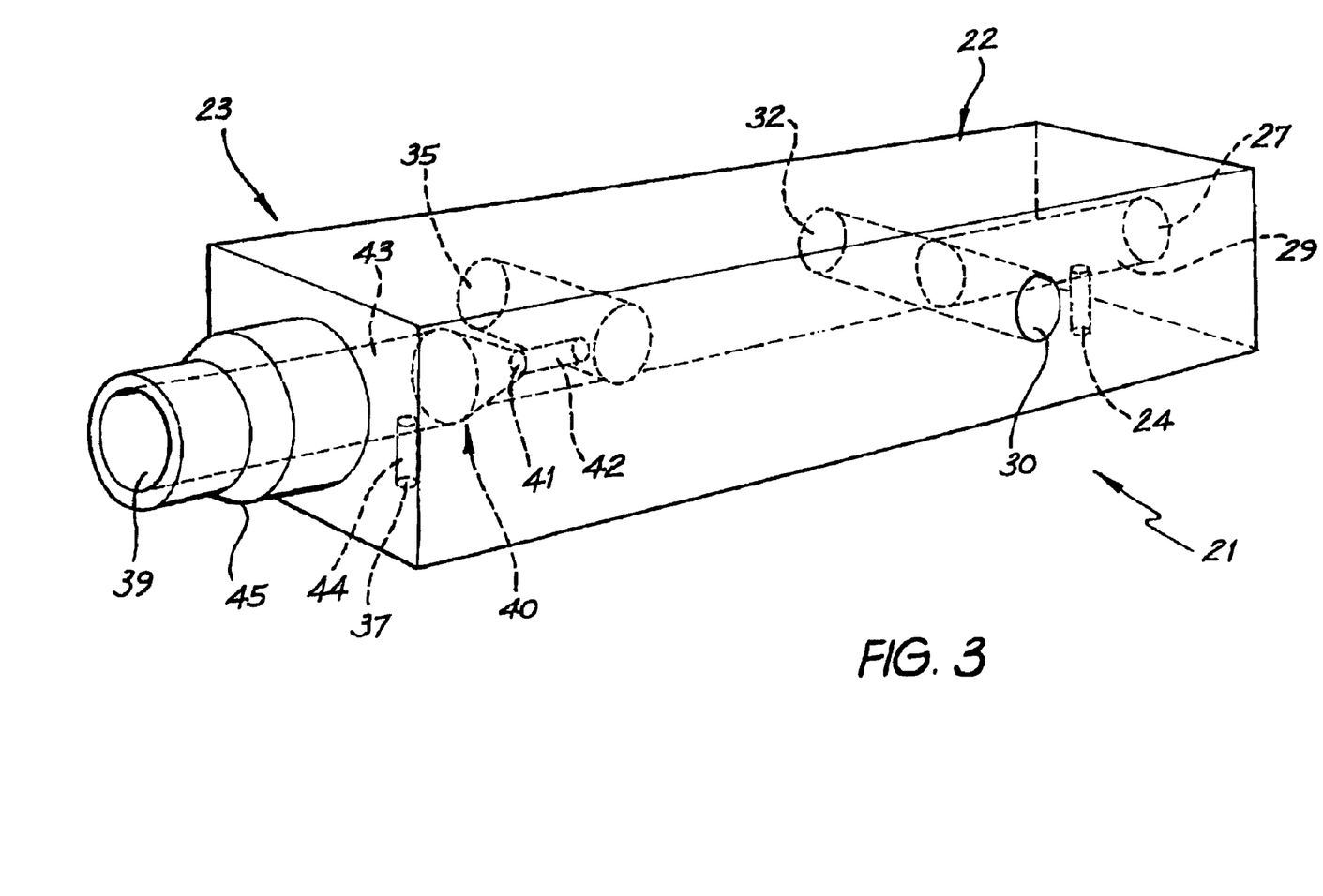
FIG. 3 is a perspective view of a connector arrangement in accordance with an embodiment of the present invention, internal structural features being shown in ghost outline.

Referring to FIGS. 2 and 3, a description will now be given of an anaesthetic supply system incorporating a connector arrangement in accordance with an embodiment of the present invention. The same reference numerals in FIG. 2 designate the same features as the supply circuit of FIG. 1, and no further description will be given of these features.

The anaesthetic supply system illustrated in FIG. 2, utilises a connector arrangement in accordance with an embodiment of the present invention, which in this example, comprises an integral cast and worked metal manifold 21. The manifold 21 has a plurality of inlets and outlets for connection to gas lines in the anaesthetic supply system.

In FIG. 3, the manifold 21 is essentially divided into two portions. These include a high pressure portion 22 for connection to gas lines at a high pressure end of the anaesthetic supply system, and a low pressure portion 23 for connection to gas lines of a low pressure end of the anaesthetic supply circuit.

At the high pressure portion 22, there is an oxygen inlet port 24 for receiving oxygen from gas line 26 leading from the regulator 2. An oxygen outlet 27 outlets oxygen to line 28 and the flowmeter 4. The oxygen inlet 24 and oxygen outlet 27 are connected by conduits 29, shown in ghost outline. In addition a oxygen flush outlet 30 connects to a line 31 and to oxygen flush valve 20 (FIG. 2). An additional oxygen outlet 32 connects to a line 33 and an additional flowmeter 34. The additional flowmeter can be used if it is required to provide oxygen to a second patient, eg a newborn infant.

In FIG. 3, the low pressure end 23, there is provided a oxygen flush inlet 35 connecting to line 36 from the flush valve 20. There is also provided a vaporiser inlet 37 for connection to the line 38 from the vaporiser 6, and a patient outlet 39 to deliver gases to the patient breathing circuit 9.

The provision of the manifold 21 in the anaesthetic supply system reduces the extent of gas lines required over the prior art supply system and allows the arrangement to be organised in a much "tidier" manner which facilitates installation service and shipping.

As discussed in the preamble, one of the problems in operation of the flush valve 20 in the prior art supply system (FIG. 1) is that relatively high pressure oxygen directly from the regulator 2 can be provided back to the outlet 8 of the vaporiser 6, resulting in damage to the vaporiser. The low pressure end 23 of the manifold 21 (FIG. 3) provides a Venturi arrangement 40 which, in this case, includes an injection orifice 41 connecting to a conduit 42 which connects to the oxygen flush inlet port 35. Injection orifice 41 opens into a broader conduit 43 leading to the patient outlet 39. A conduit 44 from the vaporiser inlet opens into the side of the conduit 43, substantially perpendicular to the flow from the injection orifice 41. In operation, when the flush valve 20 is operated, relatively high pressure oxygen introduced to the oxygen flush inlet 35 is ejected from the injection orifice 41 in a direction across the face of the internal opening of the conduit 44 into the conduit 43. This creates a Venturi effect, which results in the reduction of the pressure in line 38 between the vaporiser and the vaporiser inlet 37. This reduces the possibility of high pressure oxygen from the flush system being forced back to the outlet of the vaporiser 8.

Further, in the prior art anaesthetic supply circuits, it is usually necessary to place the pressure gauge in the patient breathing circuit with the present arrangement (FIG. 2), however, the pressure gauge 18 can be placed in the line 38 between the vaporiser and the vaporiser inlet 37. The reason for, in the prior art, placing the pressure gauge 18 in the patient breathing circuit is that there is a chance of damage due to high pressure oxygen flow on operation of the flush system. As the possibility of flow into line 38 is reduced because of the Venturi arrangement 40, this means that a pressure gauge 18 can be placed out of the patient breathing circuit as indicated in FIG. 2. This has the advantage that a single pressure gauge can be available for any type of patient breathing circuit, eg rebreathing, non-rebreathing. It is not necessary to provide a pressure gauge separately.

At the patient outlet 39 of a manifold 21 (FIG. 3), a universal outlet connector 45 is provided, for connecting to line 7 to the patient breathing circuit. Anaesthetic machine design has resulted in the standardisation of a variety of breathing circuit components and connectors. The universal outlet 45 includes a 15 mm internal diameter portion, seven eighths of an inch outside diameter portion and 23 mm outside diameter portion to take these three standard connectors.

Figure 4:
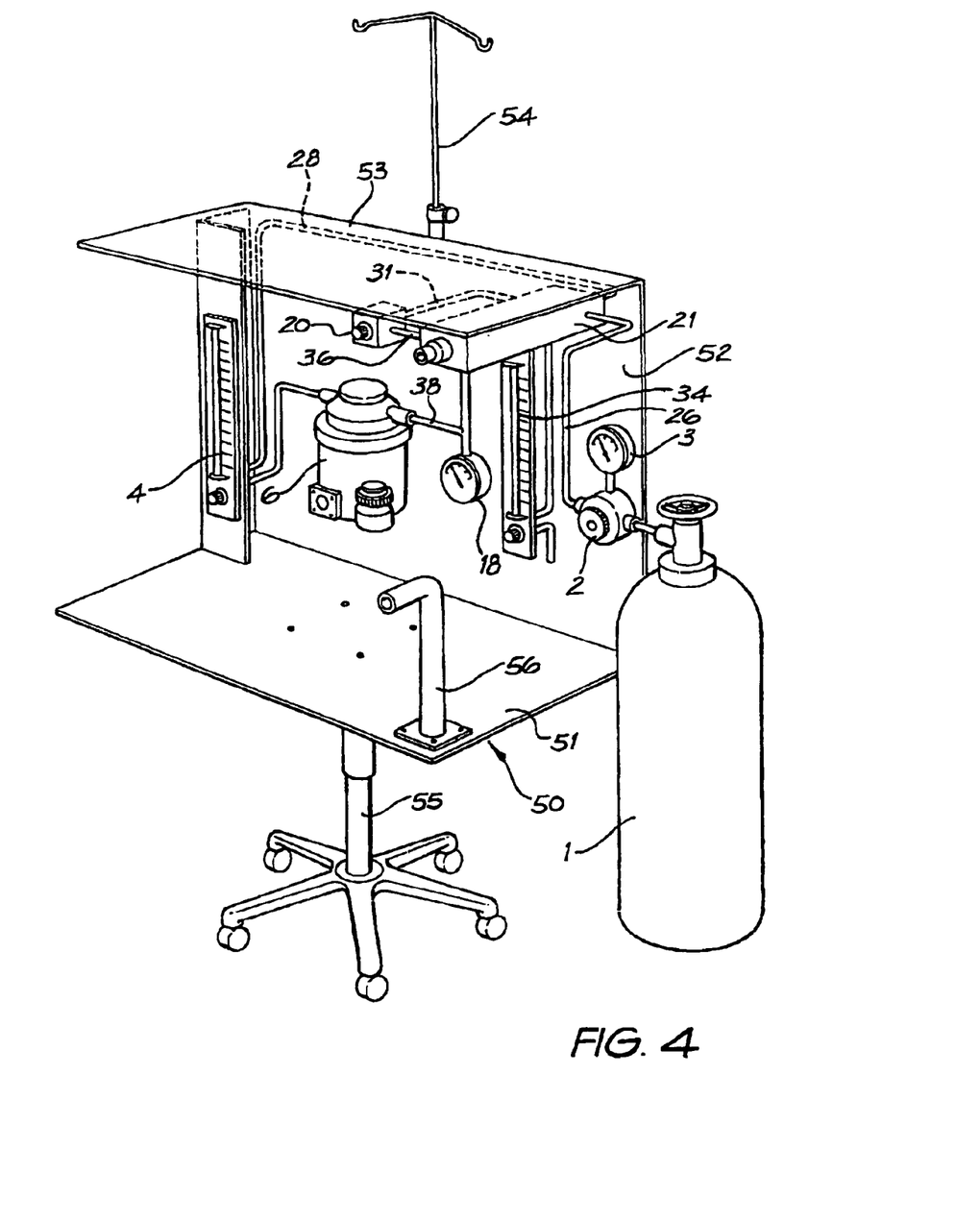
FIG. 4 is a perspective view from the front of an anaesthetic machine in accordance with an embodiment of the present invention.

Referring to FIG. 4, an anaesthetic machine in accordance with an embodiment to the present invention will now be described.

FIG. 4, the same reference numerals are used for components which have already been described in relation to FIGS. 1 and 3.

FIG. 4 discloses an "anaesthetic machine" which includes a housing including means for mounting components of an anaesthetic supply system. In this embodiment, the housing includes a support 50, comprising a base 51, a back wall 52 and a top wall 53. The base 51, back wall 52 and top wall 53 form an enclosure within which components of the anaesthetic supply system, including vaporiser 6, pressure gauge 18, flowmeter 4 and also gas flow lines 20, 38, 31, 36 and flush valve 20 are mounted, substantially shielded from the external environment. The support 50 thus protects important components and gas lines from accidental damage. In the illustrated embodiment, a manifold 21 as described above with reference to FIGS. 1 to 3 is mounted to the top wall 53 of the support 50.

It will be appreciated that the anaesthetic machine could be used without the manifold, but still protecting gas lines within the enclosure provided by the support 50. It is preferred, however, that the manifold 21 be utilised.

The "enclosed" design of the anaesthetic machine enables the machine body to be fully assembled, including vaporiser, ready for use upon removal from packaging with minimal risk of damage during shipment (all delicate components being located within the enclosure). The elimination of exposed high pressure oxygen lines to the flowmeter, oxygen flush valve etc minimises potential damage during shipment or in use (in prior art portable machines these lines are located in an exposed position at the back of the machine).

An additional advantage of the support 50 is that the top wall 53 provides a top surface which can be used as a work surface and it also acts as an elevated shelf for monitoring equipment to increase the visibility of the display.

An intravenous infusion pole 54 is attached at the back of the machine and the machine is supported upon a movable trolley 55. An additional flowmeter 34 is mounted to the top wall 53. A mount 56 for a patient breathing circuit is fixed within the enclosure supported on the base 51.

Figure 5:
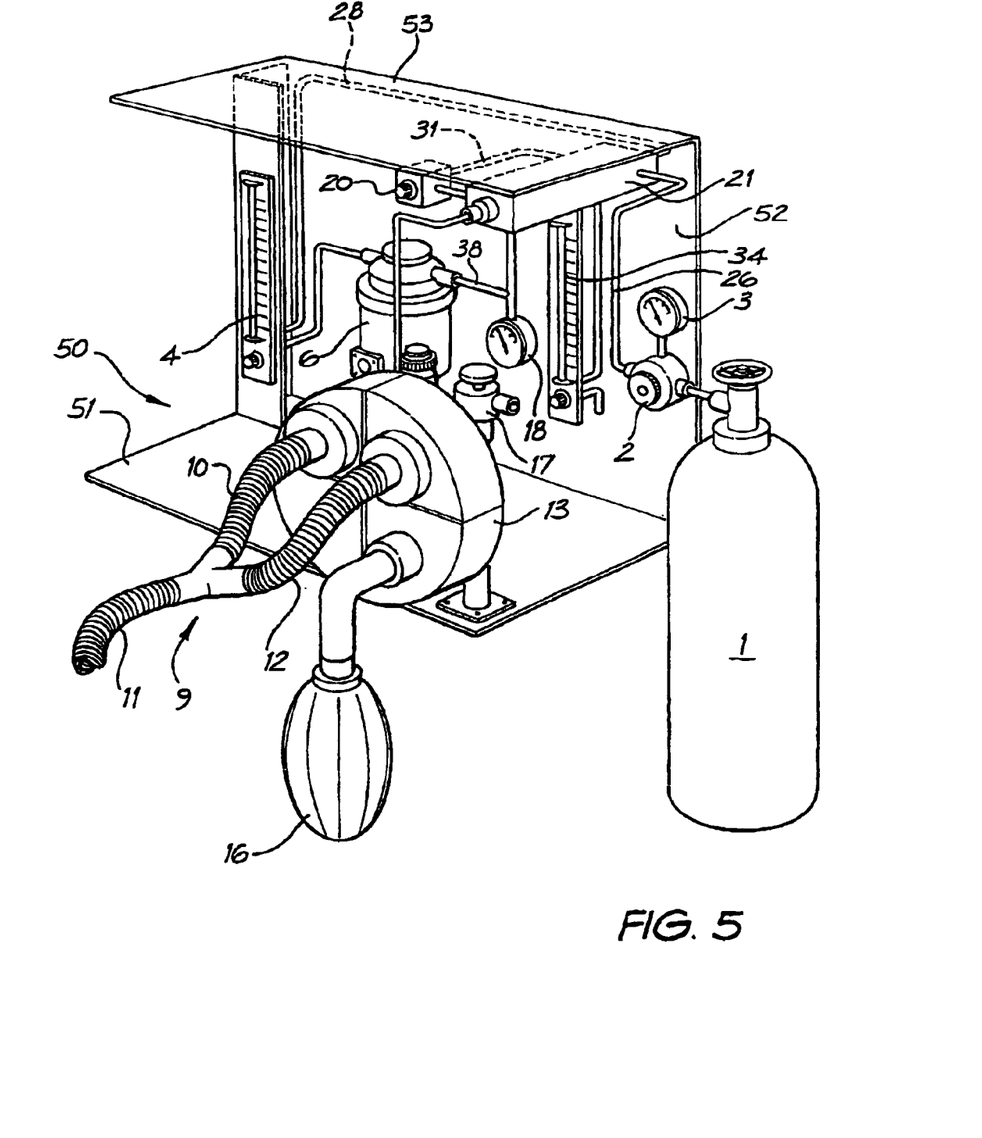
FIG. 5 is a perspective view from the front of the anaesthetic machine of FIG. 4, shown connected to a patient rebreathing circuit.

FIG. 5 shows the machine of FIG. 4 connected to a patient rebreathing circuit 9. Again reference numerals used are the same as for corresponding components shown in the other figures, and no further description will be given for the rebreathing circuit.

Figure 6:
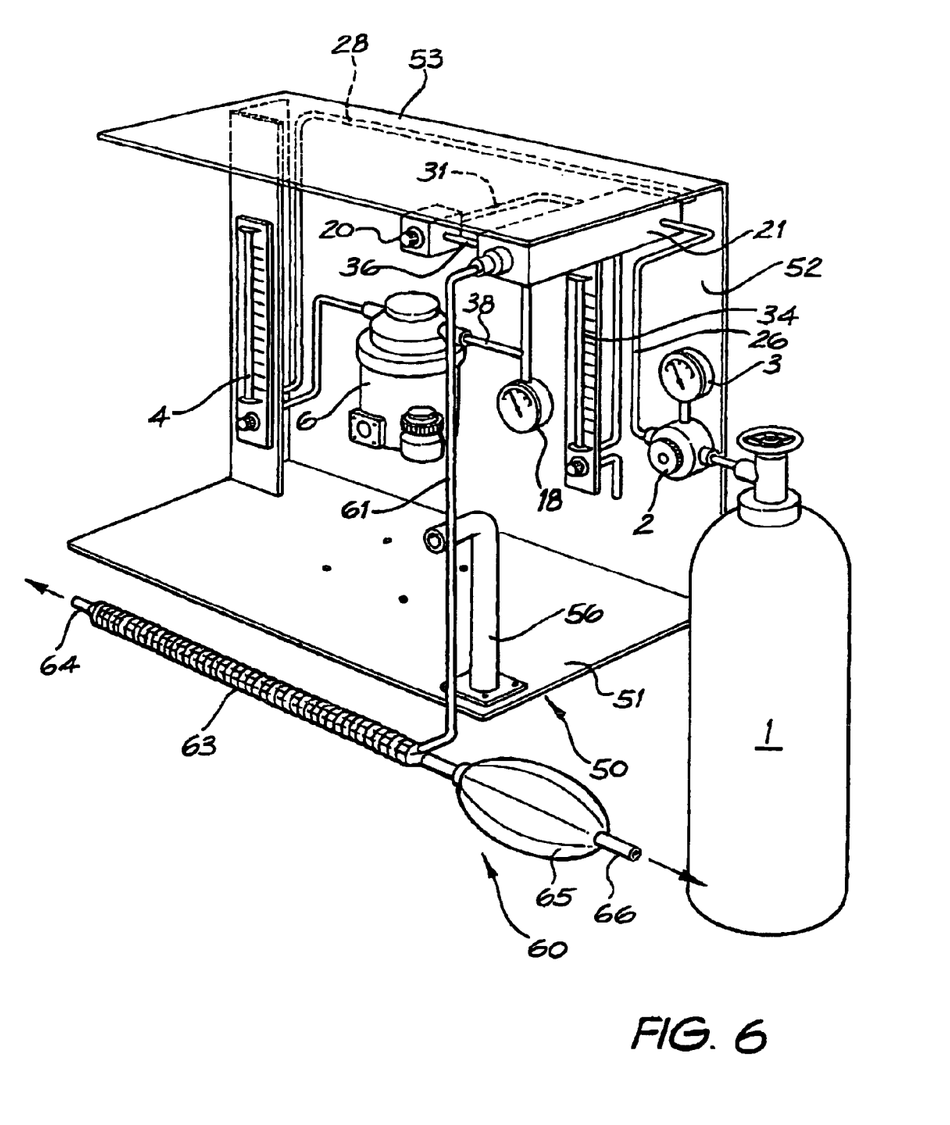
FIG. 6 is a perspective view from the front of the anaesthetic machine of FIG. 4 shown connected to a patient non-rebreathing circuit.

FIG. 6 illustrates the anaesthetic machine of FIG. 4 connected to a patient non-rebreathing system 60. The non-rebreathing system 60 includes a gas line 61 from the manifold 21 to a non-rebreathing line 23 to a patient port 24 for providing anaesthetic and oxygen to a patient. The non-rebreathing system 60 also includes a reservoir bag 65 and exit port 66 for exiting waste gases.

Figure 7:
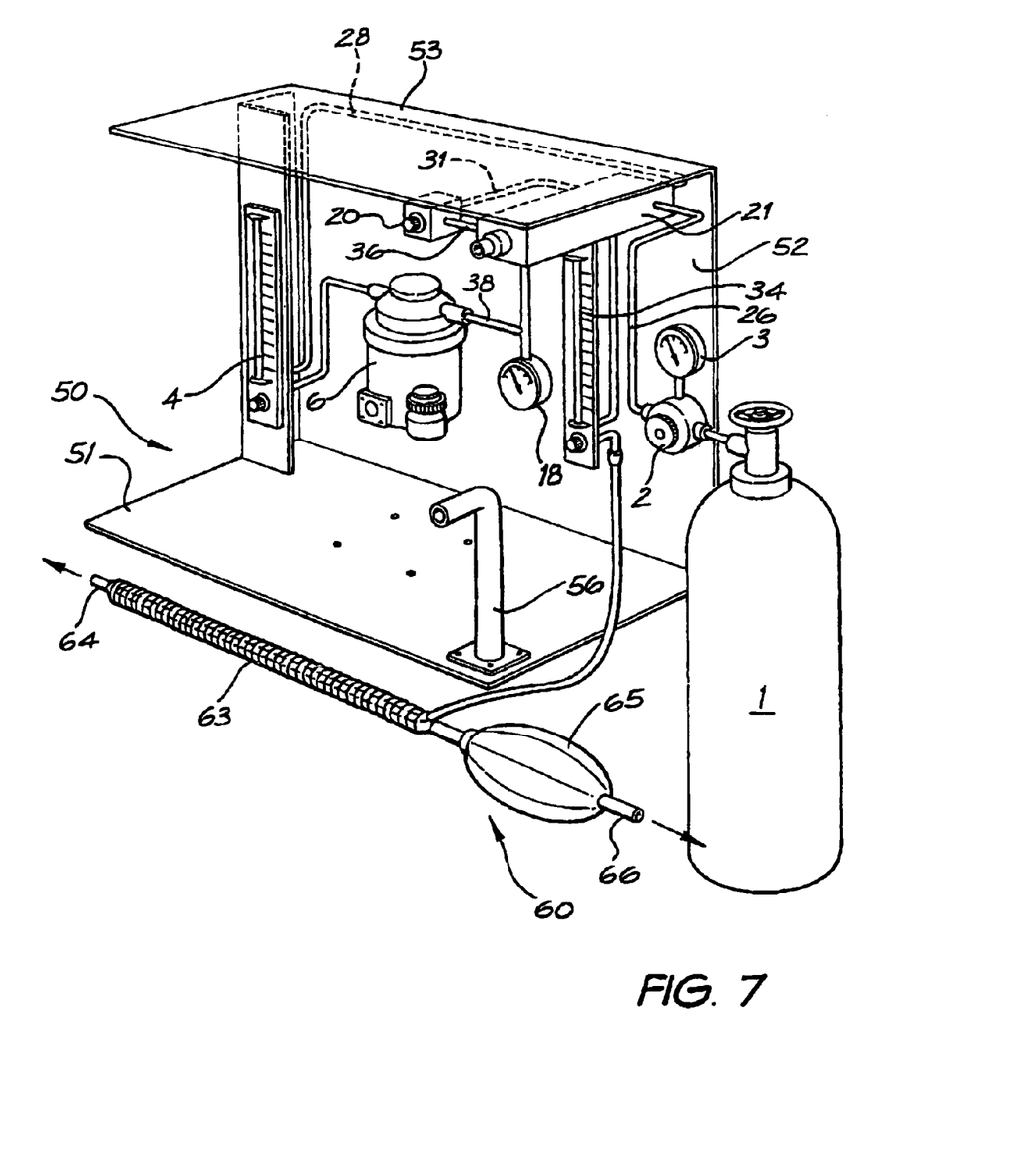
FIG. 7 is a perspective view from the front of the anaesthetic machine of FIG. 4 illustrating use of an additional flow meter.

FIG. 7 shows use of the additional flowmeter 34 via a non-rebreathing system. Pure oxygen can be provided by the additional flowmeter 34 to ventilate additional patients, eg. newborn infants.

Figure 8:
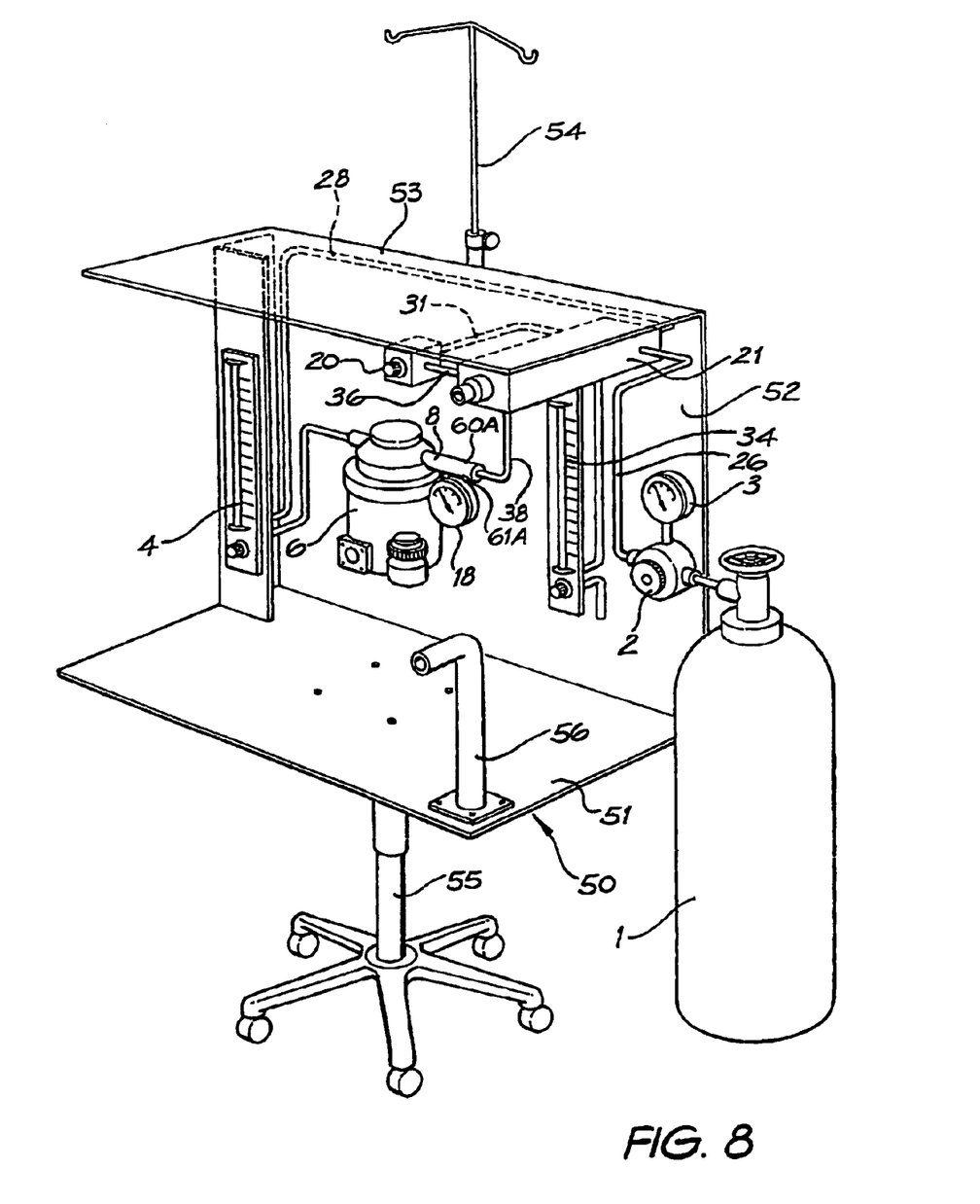
FIG. 8 is a perspective view from the front of an anaesthetic machine in accordance with a further embodiment of the present invention.

A preferred embodiment of an anaesthetic machine in accordance with the present invention is illustrated in FIG. 8. Corresponding components are given the same reference numerals as in previous drawings. In this embodiment, the pressure gauge 18 is connected directly to the outlet 8 of the vaporiser. The outlet 8 of the vaporiser is formed as a universal vaporiser outlet which includes a connection 61 for the pressure gauge.

In the embodiment described above the manifold 21 is shown as a single, integrated block. An extra arrangement could, for example, comprise two separate pieces, eg. a high pressure portion and a low pressure portion.

Note that the manifold need not be made of metal as in the above embodiment, but can be made of any suitable material.

Note that the Venturi effect need not necessarily be provided by the manifold, as described in the above embodiment.

Where the Venturi effect is required, it may be applied by a manifold with the structure discussed above, or by other apparatus.

Variations and/or modifications may be made to the invention as shown in the specific embodiments without departing from the spirit or scope of the invention as broadly described. The preferred embodiments are, therefore, to be considered in all respects as illustrative and non-restrictive.

The claims defining the invention are as follows:

1. A connector arrangement for an anaesthetic circuit comprising a manifold including a plurality of inlets and a plurality of outlets, the plurality of inlets and the plurality of outlets being arranged for connection to gas lines in the anaesthetic circuit, whereby to facilitate minimizing the extent of gas line components required in the anaesthetic circuit, the manifold including a high pressure portion and a low pressure portion only, the high pressure portion including an oxygen inlet for receiving oxygen from an oxygen supply and regulator, and an oxygen outlet for providing oxygen to an oxygen flowmeter, the low pressure portion having a vaporizer inlet for receiving oxygen and anaesthetic from a vaporizer, and a patient outlet for connection to a patient breathing circuit, for providing an oxygen/anaesthetic mixture to the patent breathing circuit; and an oxygen flush outlet provided for connection to a flush valve and an oxygen flush inlet provided for connection from the flush valve, whereby to enable the provision of a flush bypass line for enabling oxygen to be provide directly to the patient, bypassing the vaporizer, wherein the oxygen flush outlet communicates with the oxygen inlet in the high pressure portion and the oxygen flush inlet communicates with the patient outlet in the low pressure portion.

2. The connector arrangement according to claim 1, wherein the oxygen flush inlet communicates with a chamber in the low pressure portion wherein the vaporizer inlet opens into the chamber, and wherein a Venturi arrangement is provided adjacent the chamber to cause a venturi effect to occur when oxygen is passing through the oxygen flush inlet, to maintain a relatively low pressure at the vaporizer inlet.

3. The connector arrangement according to claim 1, wherein the patient outlet includes a universal connector arrangement for connecting to at least one standard patient breathing circuit line.

4. The connector arrangement according to claim 1, wherein an additional oxygen outlet is provided at high pressure portion of the manifold, and communicating with the oxygen inlet.

5. The connector arrangement for an anaesthetic circuit as set forth in claim 1 in combination with an anaesthetic machine comprising a housing including means for mounting components of an anaesthetic delivery system.

6. The anaesthetic machine according to claim 5, the housing comprising a base, a back wall and a top wall extending over the base, a back wall and top wall forming an enclosure, the means from mounting the components being within the enclosures, whereby any gas lines required to connect the components mounted in the enclosure run within the enclosure.

7. A connector arrangement for an anaesthetic circuit comprising a manifold including a plurality of inlets and a plurality of outlets, the plurality of inlets and the plurality of outlets being arranged for connection to gas lines in the anaesthetic circuit, whereby to facilitate minimizing the extent of gas line components required in the anaesthetic circuit, the manifold including a high pressure portion and a low pressure portion only, the high pressure portion including an oxygen inlet for receiving oxygen from an oxygen supply and regulator, and an oxygen outlet for providing oxygen to an oxygen flowmeter, the low pressure portion having a vaporizer inlet for receiving oxygen and anaesthetic from a vaporizer, and a patient outlet for connection to a patient breathing circuit, for providing an oxygen/anaesthetic mixture to the patent breathing circuit; and the anaesthetic circuit being used in combination with an anaesthetic delivery system; and an oxygen flow meter connected to the oxygen outlet and a vaporizer connected between the oxygen flow meter and the vaporizer inlet.

8. The anaesthetic delivery system according to claim 7, including a patient breathing circuit connected to the patient outlet.

9. The anaesthetic delivery system according to claim 7, including a pressure gauge mounted out of the patient breathing circuit.

10. The anaesthetic delivery system according to claim 9, wherein the pressure gauge is connected in the line to vaporizer inlet of the manifold.

11. A connector arrangement for an anaesthetic circuit comprising:

a manifold including a plurality of inlets and a plurality of outlets arranged for connection to gas lines in the anaesthetic circuit to facilitate minimizing the extent of gas line components required in the anaesthetic circuit, the manifold comprising:

a high pressure portion including an oxygen inlet for receiving oxygen from an oxygen supply and regulator, and an oxygen outlet for providing oxygen to an oxygen flowmeter and a vaporizer;

a low pressure portion having a vaporizer inlet for receiving a mixture of oxygen and anaesthetic from the vaporizer, and a patient outlet for connection to a patient breathing circuit, for providing the oxygen and anaesthetic mixture to the patient breathing circuit.

12. The connector arrangement for an anaesthetic circuit as set forth in claim 11 wherein the oxygen outlet supplies the oxygen from the high pressure portion of the manifold to a vaporizer circuit containing the vaporizer which mixes a desired anesthetic vapor with the supplied oxygen and delivers the oxygen and anaesthetic mixture to the low pressure portion via the vaporizer inlet.

* * * * *